United States Patent
Bedwell et al.

(10) Patent No.: US 11,420,110 B2
(45) Date of Patent: Aug. 23, 2022

(54) USER ADAPTATION SYSTEM AND METHOD

(71) Applicant: Sony Interactive Entertainment Inc., Tokyo (JP)

(72) Inventors: Gregory James Bedwell, London (GB); Daryl Cooper, San Jose, CA (US)

(73) Assignee: Sony Interactive Entertainment Inc., Tokyo (JP)

( * ) Notice: Subject to any disclaimer, the term of this patent is extended or adjusted under 35 U.S.C. 154(b) by 0 days.

(21) Appl. No.: 17/067,909

(22) Filed: Oct. 12, 2020

(65) Prior Publication Data

US 2021/0113916 A1 Apr. 22, 2021

(30) Foreign Application Priority Data

Oct. 17, 2019 (GB) .................................... 1915025

(51) Int. Cl.
*A63F 13/22* (2014.01)
*A63F 13/42* (2014.01)
*A63F 13/67* (2014.01)
*A63F 13/798* (2014.01)

(52) U.S. Cl.
CPC .............. *A63F 13/22* (2014.09); *A63F 13/42* (2014.09); *A63F 13/67* (2014.09); *A63F 13/798* (2014.09)

(58) Field of Classification Search
CPC .................................. A63F 13/22; A63F 13/67
See application file for complete search history.

(56) References Cited

U.S. PATENT DOCUMENTS

| | | | |
|---|---|---|---|
| 8,788,074 B1* | 7/2014 | Lewis | A63F 13/67 700/92 |
| 2007/0112706 A1* | 5/2007 | Herbrich | G07F 17/3274 706/21 |
| 2011/0010646 A1 | 1/2011 | Usey | |
| 2012/0197874 A1 | 8/2012 | Zatkin | |
| 2013/0288777 A1 | 10/2013 | Short | |
| 2020/0298128 A1* | 9/2020 | Yannakakis | G06N 3/0454 |
| 2020/0306638 A1* | 10/2020 | Fear | G06N 3/08 |
| 2021/0086089 A1* | 3/2021 | Pardeshi | G06N 3/04 |
| 2021/0121783 A1* | 4/2021 | Spencer | A63F 13/67 |
| 2021/0146241 A1* | 5/2021 | Bleasdale-Shepherd | A63F 13/355 |

OTHER PUBLICATIONS

Extended European Search Report for corresponding EP Application No. 20197003.5, 7 pages, dated Mar. 15, 2021.
Combined Search and Examination Report for corresponding GB Application No. GB1915025.9, 6 pages, dated Apr. 9, 2020.

* cited by examiner

*Primary Examiner* — Jay Trent Liddle
(74) *Attorney, Agent, or Firm* — Matthew B. Dernier, Esq.

(57) ABSTRACT

A method of evaluating a videogame for a first user includes: performing a calibration test using a physical input device to evaluate at least a first physical input capability of the first user with respect to that physical input device; evaluating at the at least first physical input capability exhibited with respect to that physical input device during reference play of the videogame by one or reference users other than the first user; comparing the at least first physical input capability exhibited during reference play with that of the first user; and providing an evaluation of the videogame's suitability for play by the first user, based upon the comparison.

15 Claims, 2 Drawing Sheets

USER ADAPTATION SYSTEM AND METHOD

TECHNICAL FIELD

The present invention relates to a system and method for user adaptation.

BACKGROUND

Traditionally, videogames provide entertainment through a number of mechanisms, including storytelling, visual spectacle, exploration and thrill, and also through overcoming adversity or difficulty, whether this is in an intellectual form such as solving a puzzle, or any physical form such as performing a rapid or complex sequence of moves to defeat a boss, perform a combo move or negotiate a difficult sequence of in-game obstacles.

However, unlike other forms of entertainment, sometimes the user is required to overcome such adversity or difficulty in order to access further parts of the game; consequently sometimes it can be seen as disadvantageous to limit further access to the game if the user finds a particular portion of it too difficult. For this reason, players are typically given the opportunity to save the game prior to a difficult part so they can make multiple attempts, and may also have the option to change the difficulty level of the game (for example either by allowing hints in the case of a puzzle, or reducing the amount of health of a boss, or giving the user a better shield, or reducing the number of enemies, etc.).

However, there is scope to improve upon this approach, particularly for certain groups of players who may consistently experience difficulty with such games.

The present invention seeks to make such an improvement, to mitigate or alleviate these difficulties.

In a first aspect, a method of evaluating a videogame for a first user is provided in accordance with claim 1. In another aspect, a system for evaluating a videogame for first user is provided in accordance with claim 15. Further respective aspects and features of the invention are defined in the appended claims.

BRIEF DESCRIPTION OF THE DRAWING

Embodiments of the present invention will now be described by way of example with reference to the accompanying drawings, in which.

DETAILED DESCRIPTION

Figure 1:
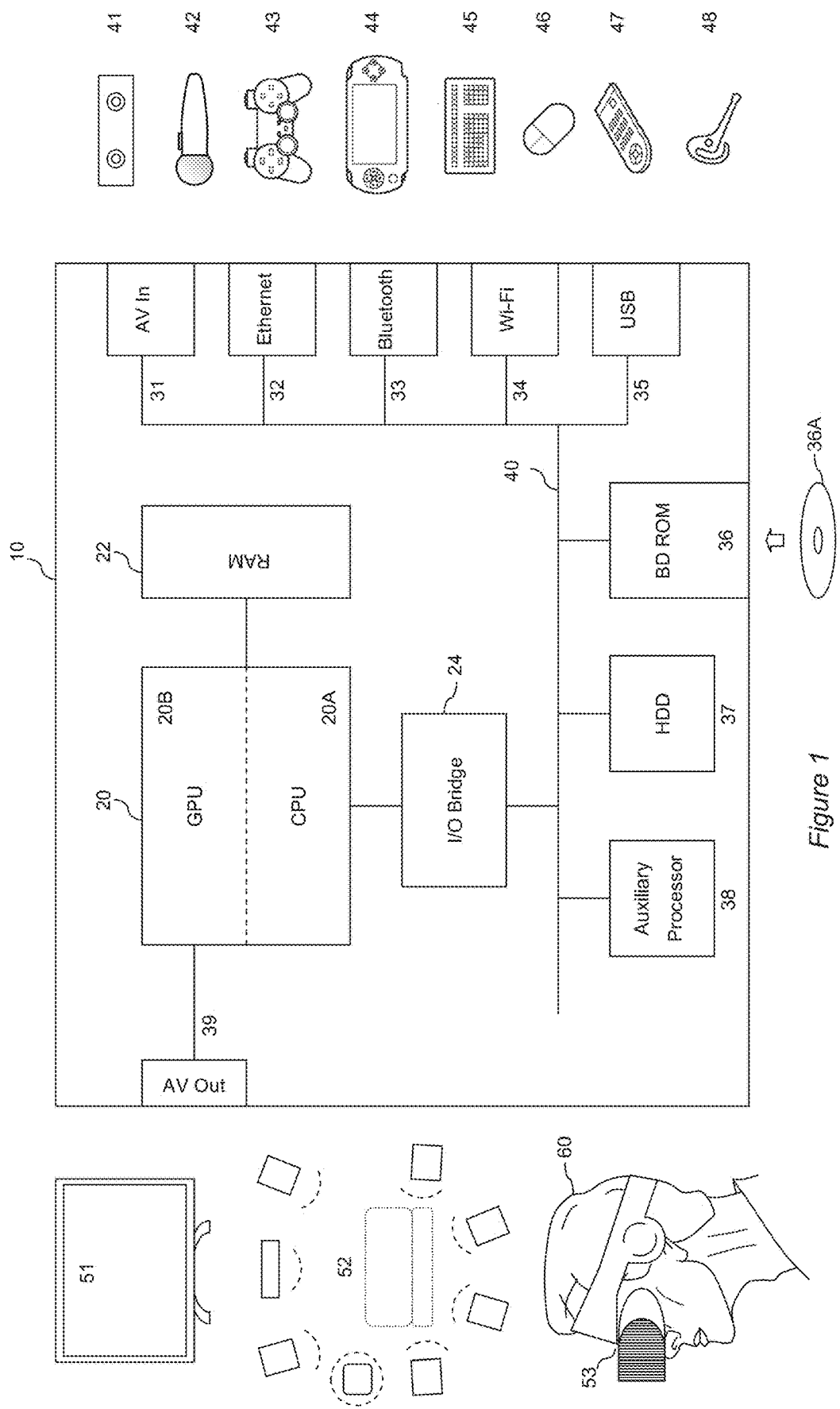
FIG. 1 is a schematic diagram of a system for evaluating a videogame for first user in accordance with embodiments of the present description.

A system and method for user adaptation are disclosed. In the following description, a number of specific details are presented in order to provide a thorough understanding of the embodiments of the present invention. It will be apparent, however, to a person skilled in the art that these specific details need not be employed to practice the present invention. Conversely, specific details known to the person skilled in the art are omitted for the purposes of clarity where appropriate.

As noted previously herein, games have been known that can have their difficulty adjusted (for example to provide easy, normal and hard settings). Furthermore, games have been known that dynamically adjust difficulty in response to the user's success in playing earlier parts of that game.

However, these approaches relate to the difficulty of the game, rather than to any difficulties the user may have when interacting with that game.

In particular, a game may require a certain degree of dexterity and/or responsiveness when using the game controller in order to play; for example, a user may need to press a button on the front of the controller (such as 'shoot'), a button on the shoulder of the controller (such as 'accelerate' or 'decelerate'), and manipulate a joystick to provide direction, either simultaneously or in quick succession (for example in a so-called combo series). This may be possible for a majority of players, but not for those with restricted movement or coordination, such as players with repetitive strain injury (RSI), arthritis, tendinitis, or other conditions that can serve to reduce dexterity and/or responsiveness, such as Parkinson's disease or Multiple Sclerosis.

As the average age of videogame players increases, this issue is likely to become more significant within the game-playing population.

Accordingly, in embodiments of the present invention a system is provided that models the input capabilities of a user, for example in terms of absolute capability and/or with reference to a notional standard user, so that users with limited capabilities can be better catered to in a game.

In an embodiment of the present invention, a user interacts with a physical input capability calibration test, which may be a game specifically designed to test input capability by requiring various common combinations of controller inputs to be activated simultaneously and/or in rapid succession, as appropriate. Similarly the calibration test may be, or may be incorporated into, a particular level of a game such as a tutorial level, which introduces input mechanics specific to a particular game. The tutorial level may be presented as such, or may simply be a level or portion of a level that first facilitates or requires use of a given input mechanic. Hence it will also be appreciated that where new input mechanics are introduced over the course of a game, then the calibration test may in effect be distributed over different levels or regions or stages of a game.

The calibration test measures one or more aspects of a user's ability to operate the input controller in response to in-game stimuli or situations.

Examples of abilities that may be tested include:
i. the ability to activate a given input on the controller, e.g. when held normally;
ii. the time taken to activate a given input on the controller in response to a triggering stimulus;
iii. the ability to activate two or more given inputs on the controller simultaneously;
iv. the time taken to successively activate two or more given inputs on the controller in sequence, and/or the time between activation of two given inputs in sequence (for example inputs that may be activated by the same digit of the user, or which may require co-ordinated movement of some or all of the hand to achieve);
v. the accuracy with which the user can control a variable input controller (such as a joystick or trigger) to provide a target input level, either alone or when also activating one or more other inputs;
vi. the ability to maintain a consistent target input level for a variable input controller, either alone or when also activating one or more other inputs;
vii. the range of hand movement available to the user when holding the controller (in terms of whole hand movement for motion control, and/or digit movement in terms of using one hand to reach a given input).

One or more of the above abilities may be tested by a suitable calibration test and suitable assignment of calibration test functions to inputs. As noted above, depending on how the calibration test is implemented, it may be that the same test function is mapped to different inputs in succession, or it may be that new inputs and functions are introduced together (for example during the course of a game).

It will be appreciated that whist reference is made herein to interactions with a controller (such as a Dual Shock 4®), the techniques herein are applicable to other physical controllers, such as one or two PlayStation Move® controllers, a joystick or flight simulation rig, a racing wheel (and any foot pedals, which may be treated like foot actuated triggers), or a mouse and keyboard. Hence 'controller' may be considered to be a general term for one or more physical controllers used in concert by a single player when interacting with a game.

As noted previously herein, the calibration test can provide as an assessment an absolute score (for example a yes/no flag for achieving specific goals such as pressing certain buttons, or doing so within certain time thresholds, and timing or accuracy values as applicable for other tests). Alternatively or in addition, the test can provide as an assessment a score relative to a notional standard user (for example again yes/no flags for achieving specific goals, and percentile timing or accuracy values relative to those of the notional standard user).

Hence for example, and with reference as a non-limiting example to a Dual Shock 4 controller, a user may be able to press the buttons marked with a cross and a triangle in sequence using their right thumb in response to an on-screen stimulus in 1.15 seconds. This may be provided as an absolute value, or alternatively maybe represented as being approximately 50% slower than the notional standard person, who can complete the same task in 0.75 seconds. Alternatively or in addition, the time taken between pressing the cross and triangle buttons may indicate a maximum speed of movement for the user's thumb, at least within the range of motion of the thumb between those two buttons.

A more complete model of the user's capabilities can be built up as more tests are conducted. The results may be used to characterise the capabilities of the user for the specific actions that have been tested; as noted above, typically these will be the actions found within a game and hence will be of immediate relevance. Furthermore, given a finite number of combinations of user input for a videogame controller, and where the most common combinations of user input may be known from user telemetry, then the calibration test may be designed to obtain measurements for the most common combinations, making the results relevant to a large number of games, even if these are not known in advance of the test.

Alternatively or in addition, some or all of the calibration test results may be used to generate a more general model of the user's dexterity. In this case, the absolute or relative values from the calibration test can be used to characterise an absolute or relative range of movement of one or more digits of the user's hand, and also an absolute or relative speed of movement of one or more digits of the user's hand; these variables may also be interdependent, so that the speed of movement depends upon the current position of a digit within the range of movement, and similarly the available range of movement may vary with speed (for example where a user requires a slower stretch or whole hand movement to reach certain controls).

Typically such a dexterity model will include the user's thumbs, as typically these interact with inputs on the upper surface of the controller. Optionally the model may include the user's index fingers, which typically interact with inputs on the shoulder of the controller (inputs on the side surface of the controller facing away from the user). Further optionally the model may include the user's middle fingers, which may also interact with inputs on the shoulder of the controller. Further optionally the model may include the remainder of the user's hand, typically as a function of position/orientation and optionally also speed to achieve such positions/orientations. It will be appreciated that the order, detail, and/or extent of the model may depend upon the type of controller(s) that the user is interacting with.

This model may be generated by extrapolating from certain tasks in the calibration test; as a non-limiting example, for a conventional handhold on a controller, different actions will represent movements of the user thumb(s) in an XY plane over the surface of the controller, together with movements in Z direction to activate certain controls. Hence calibration test tasks can build a partial map of movement and/or speed of the thumb over the surface of the controller from which more general movement over the controller can be inferred. Similarly, speed and accuracy of actuation of trigger controls on the shoulder of the controller can be measured, for different degrees of actuation, to at least partially model the behaviour of the user's index finger(s), from which a more general movement of the index finger can be inferred. Again the variables may be interdependent, with for example accuracy depending on both speed and degree of actuation. It will be appreciated that this approach can be used for other aspects of controller function as well, such as range and speed of motion for whole hand or paired hand positioning of the controller for motion control. Again such variables may be interdependent, with speed depending on position and/or orientation and vice-versa. Again, it will be appreciated this approach can apply to other forms of controller, such as mouse movement and clicks, or acceleration/brake control using foot pedals.

Optionally, the direct results of the calibration test(s) and/or a generalised model of some or all of the user's hand (or other body part used for control) may be used to categorise the user's capabilities (for example based on expected ranges associated with categories), with an overall category related to a type of capability (for example, restricted range, restricted speed, restricted accuracy), and optionally a score for that category, either as a value or as another classification (e.g. none, low, moderate, high, or near-typical), or similarly subcategories for each overall category.

Optionally, the generalised model may be generated using a machine learning system that has been trained on a partial set of inputs (representative of those in the calibration test) using a target that either represents a more complete range of movements (such as may be obtained using clinical testing) or the parameters of a general model thereof, and/or a classification of the user's capability similar to that described previously herein.

Hence as described herein, in summary the dexterity of one or more digits of the user's hands (and optionally the hands themselves and/or another body part used for physical interaction with a controller) is evaluated by completing one or more tasks in a calibration test, which itself may be a specific (e.g. stand-alone) calibration test/game, or may be a level or part thereof within a conventional game that is adapted to implement the techniques described herein. This evaluation may optionally be generalised on the basis that it represents a partial sampling of the overall dexterity of the user from which the more general representation of their dexterity can be inferred/extrapolated. This may be done based on the absolute or relative values themselves, using extrapolation/inference rules and heuristics, or by using a suitably trained machine learning model. Alternatively or in addition, the evaluation may optionally be used to generate one or more classifications of user capability, again based either on the absolute or relative values themselves, by using appropriate rules or heuristics or by using a suitably trained machine learning model.

In any event, the obtained characterisation of the user's physical input capabilities (such as specific absolute or relative values for individual actions, and/or as one or more generalised dexterity models, and/or as one or more capability classifications) may then be used to evaluate a target videogame to determine its relative difficulty for that user.

This may be achieved for example by using gameplay telemetry from that target videogame, for example from alpha and/or beta testers, and/or optionally from early gameplay upon general release, to obtain capability data for a notional standard user for actions equivalent to those in the configuration test, or a subset thereof. The notional standard user may for example be an average of a cohort of testers and/or early adopters, or results from a representative sample thereof. Alternatively a model of a notional standard user who can be assumed to be representative of the majority audience with typical input capabilities may already be available.

An individual user's capability may then be modelled relative to this using any of the techniques above, using this notional standard user as the benchmark.

Alternatively to represent the game, an average of a cohort of testers and/or early adopters or results from a representative sample thereof may be compared against a separate notional standard user (for example based upon a cohort of testers who interacted with the calibration test), and the relative difference between the apparent dexterity used by representatives of the game and the current user can be compared. Hence for example beta testers for a game may have higher dexterity scores than the notional standard person, whilst the example user may have lower dexterity scores. In this particular case it may be that the developer of a game may wish to alter the game so as to reduce the dexterity requirements to be closer to the notional standard person in any case; as will be described below, they may therefore wish to provide several tiers of reduction to accommodate different levels of capability.

In either case, this comparison may be implemented for one or more specific absolute or relative values for individual actions, and/or for one or more generalised dexterity models, and/or for one or more capability classifications.

By way of example, a particular level in a game may comprise a mixture of exploration and combat, where combat is with a random distribution of different creatures encountered as the user explores the game environment. In addition, in order to progress to a new environment, the player must defeat a particular creature.

Telemetry from playing this game may be used to indicate the required dexterity to play the game, optionally not just in terms of an overall requirement, but instead or in addition in terms of a distribution of time. In other words, 90% of gameplay may involve relatively low dexterity, for example during exploration. Meanwhile a further 5% of the game play may involve moderate dexterity whilst combating relatively easy creatures, 4% of the game play may involve relatively high dexterity whilst combating relatively difficult creatures, and 1% of the game play may involve relatively very high dexterity whilst combating the particular creature that is blocking progress.

The indicated dexterity could be compared against the user's model, again either in terms of specific input functions, a generalised model, or a corresponding capability classification, to determine if dexterity levels are above those that the user is capable of (or comfortable with).

The result may then be presented for example in a traffic light system, perhaps in this case a pie chart or similar summary graphic showing 95% green, 4% amber and 1% red, where 95% of the game is likely to be within the user's dexterity capability, 4% is likely to be at or near the limits of the user's dexterity capability, and 1% is likely to be above the user's dexterity capability.

Optionally, such a traffic light system may also be displayed on a timeline; this is likely to show that the 1% is at the end of the level and hence indicative of a problem that may limit progress for the user. This may be particularly true if the results are based on a cohort of users playing the game, or an average of representative players; this is more likely to show moments which are consistently difficult for the users. It will be appreciated that where different reference players complete a level at different times, respective time lines can be normalised, and optionally averaged.

Alternatively or in addition, such a traffic light system may be displayed on a map of the game environment, thereby indicating to the user where particularly difficult challenges or encounters are likely be found; this may be of assistance for example so that a user can plan when to visit a particular area: for example when they have a friend available to provide physical assistance. Other segmentations of a game may depend on character class, quest chosen, or the like Similarly, the entire game can be summarised with a traffic light or other scoring metric to indicate how likely the user will be able to satisfactorily interact with the game. Where different difficulty levels are provided by the game, different traffic lights may be provided for different difficulty levels. The traffic light or equivalent score may be based on a weighted sum of in-game traffic light values; hence in the example above, the overall assessment may be amber despite most of the game being green. Alternatively or in addition, the worst-case score can be provided, which in this case would be 1% red, i.e. 1% of the game is likely to be outside the capability of the user.

Such an assessment scheme may then be used for example to rank games already owned by the user (for example within a virtual library), or to rank games within a store, for example based on weighted average or % in red; similarly, alternatively or in addition such an assessment scheme may be used to filter games already owned by a user, or listed within a store. Hence a user may be able turn a rank or filter on or off to see what games may be appropriate for play. Such a ranking or filtering may be enabled, updated on the basis of any new user calibration, or disabled, according to a user's wishes.

Updating a filter or ranking when a new user calibration is provided may be of use if a user's condition is becoming either progressively worse, or progressively better. Meanwhile being able to turn a filter on or off assists those users who have sporadic or recurrent conditions such as tendonitis, or those users wish to play within a comfortable range of motion (whilst nonetheless being able to play with greater dexterity for brief periods), and so may which to access either a full game selection or a filtered one depending on how they feel.

Similarly, alternatively or in addition a suitable difficulty level may be advised for a game where different difficulty levels have been given different scores, and again games may be ranked or filtered on the basis of different difficulty levels (such as for example a game may be treated as three separate games for ranking or filtering purposes for its built-in easy, medium and hard difficulty settings).

In addition to helping users assess games, the above assessments may be used to assist developers; user calibration results/capability data for one or more users, or typically a plurality of users with varying levels of dexterity may be acquired, as described previously either based on a calibration test that models common modes of interaction that may be applicable to a specific game, or based on a calibration test using that the some parts of the developer's game itself.

A developer may then identify what parts of their game may prove difficult to certain users or classes of users, to enable them to decide whether or not to either modify the game to be more inclusive of these users, or to modify at least one difficulty level to be more inclusive of these users or user classes, or a chosen proportion thereof. Hence, for example, a developer may choose to adapt the 'easy' difficulty level so that it does not generate a red traffic light for a given class of users with a given limited capability/dexterity.

Alternatively or in addition, to accommodate an individual user's needs, the game may respond to their individual dexterity/capability as indicated by a calibration test (as described previously herein, either as separate calibration test or incorporated into the game itself).

This may be done in one or more of a number of ways.

Firstly, the calibration test may indicate specific inputs or input sequences with which the user has difficulty; where these are used within the game, the game may provide the option to remap the controls, either to different buttons, or a different sequence, that the user is better at inputting, and/or change any threshold used for error tolerance or speed of activation of these inputs are input sequences. Alternatively or in addition, the game may provide the option to auto-input a particular sequence at key moments where this is necessary to progress the game. Alternatively or in addition, the game may reduce, limit or suspend damage taken by a player during periods of the game that have a high prevalence of an input or input sequence with which the user has difficulty. Alternatively or in addition, the game may provide an 'auto destruct' function for enemies, for example to kill all enemies currently on screen or within a given radius of the player (accessible for example via a pause menu, to avoid accidental selection). Alternatively or in addition, the game may allow the user to skip, e.g. teleport, to a subsequent safe point (such as a predetermined save point), thereby bypassing a portion of the game with which they have difficulty. Anyone or more of these facilities, or any other facility apparent to the skilled person that mitigates a user's difficulties with their physical input capability, may be enabled for any user whose performance with the calibration test indicates that they have reduced capability/dexterity compared to the notional standard user.

The number or extent of mitigating features may be proportional to the degree of reduction in capability dexterity, or the type of reduction in capability/dexterity (e.g. class or classification of limitation). Similarly the number or extent of mitigating features may use used throughout a game or may vary within the game, for example in a similar manner to the time-based traffic light system described previously herein; the developer may evaluate levels, regions, quests, enemies or any suitable component of the game for which interactions are expected with respect to the standard notional user, enabling individual evaluation of these interactions with respect to an individual user's capability data, based on relative capability with respect to the standard notional user. Subsequently one or more of the above mitigating features may be used where optionally one or more of a respective level, region, quest, enemy or any suitable component against which interaction is expected is encountered that would trigger a red traffic light or equivalent indicator that the interaction is beyond the reasonable capabilities of the user.

Optionally, where a mitigating feature is activated, any suitable graphical notification may be added to the screen to indicate that this has happened; this would help to prevent users intentionally creating or using a user capability data file indicative of limited dexterity to obtain an unfair advantage for example when attempting a speed run or competing in e-sports. Similarly, a graphical indication of the user is benefiting from mitigating feature may be provided in association with their avatar within a multiplayer game, and/or users benefiting from mitigating features may be preferentially placed within the same instance of a multiplayer game, optionally with players using similar mitigating features preferentially placed within the same instance of a multiplayer game.

Hence in summary embodiment of the present description enable the physical interaction capabilities of the user to be evaluated, either on an absolute basis or relative to a notional standard user, to provide information on their physical capability with respect to specific inputs are input sequences, and/or a general model of their dexterity, and/or a classification that in turn may be associated with a class-based general model of dexterity.

In turn, the evaluation may be used to rank or filter the user's own games, or games recommended to the user.

The user's capability data, or a corpus of such evaluation data (or generalised evaluations for one or more classes of capability) may be used by a developer to evaluate the difficulty of their game or of a difficulty setting in their game for the user or that class of user, to enable modification of the game during development.

Similarly, user capability data may be used to trigger one or more features of the game that serve to mitigate limitations in dexterity and/or input capabilities of the user. This may be done for the whole game as if to create a custom difficulty mode, or may be done at the individual's own, region, enemy, etc., level where this granularity of notional standard player reference data is provided.

Where the game play is modified to assist a user who has limited input capability/dexterity, optionally this is indicated graphically within the game so that a viewer of a recording of the game, or other players sharing a multiplayer game, are aware that a modification has occurred. In the case of multiplayer games, users with reduced input capabilities or dexterity may be preferentially matched to the same game instance.

Figure 2:
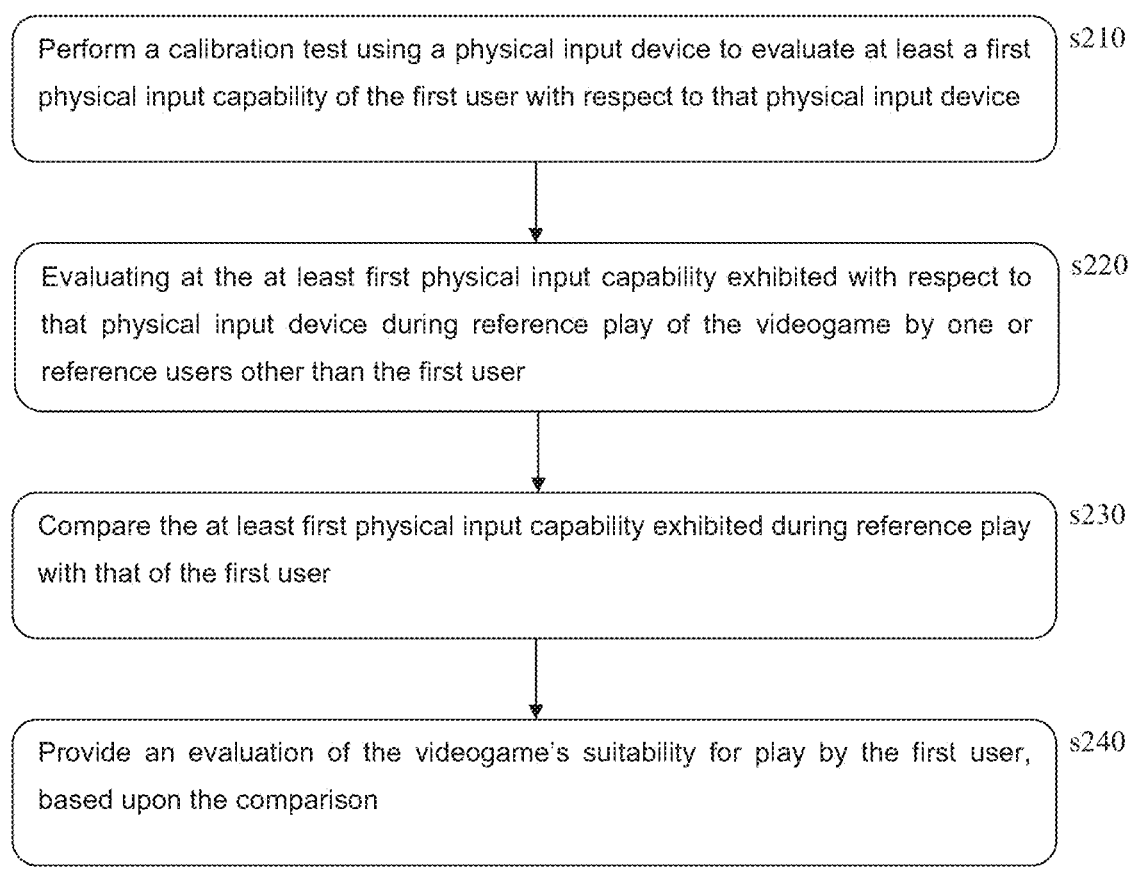
FIG. 2 is a flow diagram of a method of evaluating a videogame for a first user in accordance with embodiments of the present description.

Referring now to FIG. 2, in a summary embodiment of the present invention a method of evaluating a videogame for a first user comprises in a first step s210, performing a calibration test using a physical input device (for example a handheld controller such as the dual shock four or PlayStation Move controller, or a steering wheel, foot pedals, or other physical input device) to evaluate at least a first physical input capability of the first user with respect to that physical input device (for example their ability to reach and activate inputs or sequences of inputs, or their speed to do so, as discussed previously herein).

A second step s220 then comprises evaluating at the at least first physical input capability exhibited with respect to that physical input device during reference play of the videogame by one or reference users other than the first user. As discussed previously herein, reference users are typically users of average capability such as the developers, beta testers or early adopters, who may play through the game and the physical input capability they exhibit whilst playing the game (for example in reaching and activating inputs or sequences of inputs, or their speed to do so) can be similarly evaluated.

It will be appreciated therefore that play through of a game by reference users will capture the physical requirements of normal play during the course of game, for example in terms of speed, dexterity, range of motion, and the like as discussed elsewhere herein. This in turn provides a basis for comparison with the physical abilities of the current user for play of corresponding parts of the game, and hence what parts of the game fall within the likely abilities of the player. As discussed elsewhere herein it can then be possible to determine what proportion of the game fits within the user's abilities (or conversely does not), or what sections of the game may be outside the user's ability (for example, the last couple of levels of a game may be more difficult, but this may be okay with the user because, like many players, they don't expect to reach the last few levels), to assist the user with evaluating the desirability of playing the game. It also provides the game with information about when it may be appropriate to offer or implement mitigating actions to assist the user, for example so that the game behaves normally when it is within the users abilities, but only offers or engages mitigating actions for levels or parts of a game judged to be challenging to the user.

It will be appreciated that whilst new games may be evaluated for this purpose by the developers, there is a large library of legacy games available; optionally, the operating system of the videogame console, or a helper app or similar may operate to evaluate the physical input capabilities exhibited by a user playing a legacy game (for example using telemetry from existing players, or by using a dedicated panel of one or reference players). Whilst it may not necessarily be possible to provide a detailed assessment of the physical requirements for individual parts of the game (though this may be the case if a complete run through can be collated from capture plays), at least overall physical input capability requirement may be established, based upon evaluations from one or more players of such legacy games. In this way, evaluations for these legacy games may effectively be crowd sourced from existing players of these games.

A third step s230 then comprises comparing the at least first physical input capability exhibited during reference play with that of the first user. As discussed previously herein, this can identify physical input capabilities of the types discussed here that are used when interacting with the game and that the user has difficulty with or is incapable of performing.

Then a fourth step s240 comprises providing an evaluation of the videogame's suitability for play by the first user, based upon the comparison. Again as discussed previously, this is likely to relate to the extent to which the user has difficulty with or is incapable of performing physical inputs used when playing the game.

In an instance of this summary embodiment, the physical input capability of the first user is categorised based upon the evaluation. As described previously herein, optionally developers can provide mitigating features or set levels to accommodate different categories of user, and so categorising the user may assist with selecting a predetermined level. Similarly games may be ranked or reviewed based on such categories, again assisting a user.

In an instance of this summary embodiment, the evaluation of the at least first physical input capability exhibited during reference play of the videogame is assumed equivalent to a notional standard physical input capability. Hence as previously described herein, rather than playing through the videogame and assessing it directly, it may be assumed that the videogame is suitable for a notional standard user with a notional standard physical input capability; this physical input capability may be used instead of a direct assessment of the videogame. This may be of use to enable any filtering or ranking mechanism for a library or store of games to also operate upon legacy games that have not been specifically evaluated according to the techniques described herein.

In an instance of this summary embodiment, separate evaluations of the videogame's suitability for play by the first user is performed for each of two or more difficulty levels of the videogame. Similarly, alternatively or in addition separate evaluations of the videogame's suitability for play by the first user may be performed for different modes of play (such as single player versus multiplayer, or survival versus creative mode), and similarly individual downloadable content packs (known as 'DLC') may be separately evaluated where these provide new or alternate gameplay.

In an instance of this summary embodiment, an evaluation of the videogame's suitability for play by the first user comprises an evaluation of physical input capability difficulty relative to the user's physical input capability. As noted previously herein, this may relate to relative ability and/or speed of access to particular inputs or sequences used within the game between the first user and the reference user or a notional standard user, or may relate to the comparative capability of the first user and the reference user or notional standard user within more general models of their input capabilities, or may relate to the comparative capability of a class or category to which the first user belongs relative to the reference user or notional standard user. Where there are no differences, then the first user may be deemed capable of playing the game or the relevant part thereof; where there are differences, these may either provide a continual scale of increased difficulty relative to the user's normal capabilities, or one or more thresholds may be provided to indicate input capability requirements that may be difficult or uncomfortable for the user, and and/or to indicate input capability requirements that may be impossible for the user.

In an instance of this summary embodiment, an evaluation of the videogame's suitability for play by the first user comprises one or more selected from the list consisting of:
  i. an evaluation of the proportions of the game evaluated to be at respective physical input capability difficulties;
  ii an evaluation of respective physical input capability difficulties at a plurality of time or progress intervals during a game; and
  iii. an evaluation of respective physical input capability difficulties at a plurality of locations within a game.

As noted above, a reference play through of the game by one or more reference players provides information about the expected physical abilities used during play, and this can be compared to the first user's physical abilities to determine at what point during play the expected physical abilities exceed those of the first user (for example by threshold amount); the proportion of the game in which this occurs may be evaluated to suggest how often the user will be frustrated, and/or when during the game or how far along the game this occurs may also be determined. For games which do not follow a linear progression, this may translate to the identification of areas within the game that are particularly challenging, for whatever reason.

Typically, the respective physical input capability difficulties may be represented by values on a continual scale of increased difficulty relative to the user's normal capabilities, or by a threshold system, such as a traffic light system described previously herein.

In an instance of this summary embodiment, the calibration test is an interactive activity run separate to the videogame. As noted previously herein, the test may be separate to the videogame (which may be of use in support of legacy videogames or videogames not directly implementing any of the techniques described herein), or may be a specific part of a videogame such as a tutorial, or may be distributed within the videogame as different inputs are introduced.

In an instance of this summary embodiment, the method comprises the step of defining a difficulty mode for a videogame that is within a threshold physical input capability difficulty for the first user or a category of users to whom the first player belongs. This may be implemented for example by a developer when choosing changes to in game parameters or other aspects of the game associated with a particular difficulty level such as an 'easy' level. Optionally a developer may also provide one or more difficulty levels that are only unlocked in response to a calibration test indicating that a user has physical input capability difficulties or belongs to a particular category for which a difficulty level has been created.

Instance of this summary embodiment, the method comprises the steps of evaluating the videogame's current suitability for play by the first user during gameplay; and if the videogame's current physical input capability difficulty relative to the physical input capability of the user is above a predetermined threshold, implementing an in-game mitigation of that difficulty. As described herein, the current suitability can relate to a current level, a current location, a current quest, or current enemy, or similarly could relate to a current in game equipment loadout, or character class or the like, where these may affect how a player interacts with the game.

In such a case, then as described previously herein, the in-game mitigation may comprise one or more selected from the list consisting of:
 i. remapping one or more in game controls to a different physical input or sequence of inputs;
 ii. increase a threshold for error tolerance, or speed of actuation of an input or sequence of inputs;
 iii. auto input a predetermined sequence at a predetermined moment within the game;
 iv. reduce, limit or suspend damage taken by the user;
 v. provide an auto destruct function for in game obstacles;
 vi. allow the user to progress to a predetermined safe point.

Similarly in such a case, then as described previously herein a graphical indication that an in-game mitigation is being implemented is included with the videogame display to inform anyone watching the game play, or in the case of a multiplayer game, to inform other players, that a mitigation is in use.

In an instance of the summary embodiment the availability of a videogame for selection by the user is responsive to the evaluation of the videogame's suitability for play by the first user. As described previously herein the availability may relate to the game's position within a ranking of games, and/or may relate to whether a game is filtered in or out of a list of games, within the users own game library or a recommendation list, search result, storefront, etc.

It will be appreciated that the above methods may be carried out on conventional hardware suitably adapted as applicable by software instruction or by the inclusion or substitution of dedicated hardware.

Thus the required adaptation to existing parts of a conventional equivalent device may be implemented in the form of a computer program product comprising processor implementable instructions stored on a non-transitory machine-readable medium such as a floppy disk, optical disk, hard disk, solid state disk, PROM, RAM, flash memory or any combination of these or other storage media, or realised in hardware as an ASIC (application specific integrated circuit) or an FPGA (field programmable gate array) or other configurable circuit suitable to use in adapting the conventional equivalent device. Separately, such a computer program may be transmitted via data signals on a network such as an Ethernet, a wireless network, the Internet, or any combination of these or other networks.

In this regard, an example of a system for evaluating a videogame for a first user may be a Sony PlayStation 4 ® entertainment device operating in conjunction with any suitable physical input device. Such an entertainment device may be used by the first user to perform their calibration test. Similarly the entertainment device or an equivalent device (such as a PlayStation 4 belonging to the game developer) may be used to evaluate the videogame by one or more reference users, or to establish the physical input capabilities of a notional standard user. Such an entertainment device may then perform the comparison and provide an evaluation of the videogame's suitability for play by the first user based upon that comparison.

Referring now to FIG. 1, this schematically illustrates the overall system architecture of a Sony® PlayStation 4® entertainment device. A system unit 10 is provided, with various peripheral devices connectable to the system unit.

The system unit 10 comprises an accelerated processing unit (APU) 20 being a single chip that in turn comprises a central processing unit (CPU) 20A and a graphics processing unit (GPU) 20B. The APU 20 has access to a random access memory (RAM) unit 22.

The APU 20 communicates with a bus 40, optionally via an I/O bridge 24, which may be a discreet component or part of the APU 20.

Connected to the bus 40 are data storage components such as a hard disk drive 37, and a Blu-ray® drive 36 operable to access data on compatible optical discs 36A. Additionally the RAM unit 22 may communicate with the bus 40.

Optionally also connected to the bus 40 is an auxiliary processor 38. The auxiliary processor 38 may be provided to run or support the operating system.

The system unit 10 communicates with peripheral devices as appropriate via an audio/visual input port 31, an Ethernet® port 32, a Bluetooth® wireless link 33, a Wi-Fi® wireless link 34, or one or more universal serial bus (USB) ports 35. Audio and video may be output via an AV output 39, such as an HDMI port.

The peripheral devices may include a monoscopic or stereoscopic video camera 41 such as the PlayStation Eye®; wand-style videogame controllers 42 such as the PlayStation Move® and conventional handheld videogame controllers 43 such as the DualShock 4 ®; portable entertainment devices 44 such as the PlayStation Portable® and PlayStation Vita®; a keyboard 45 and/or a mouse 46; a media controller 47, for example in the form of a remote control;

and a headset 48. Other peripheral devices may similarly be considered such as a printer, or a 3D printer (not shown).

The GPU 20B, optionally in conjunction with the CPU 20A, generates video images and audio for output via the AV output 39. Optionally the audio may be generated in conjunction with or instead by an audio processor (not shown).

The video and optionally the audio may be presented to a television 51. Where supported by the television, the video may be stereoscopic. The audio may be presented to a home cinema system 52 in one of a number of formats such as stereo, 5.1 surround sound or 7.1 surround sound. Video and audio may likewise be presented to a head mounted display unit 53 worn by a user 60.

In operation, the entertainment device defaults to an operating system such as a variant of FreeBSD 9.0. The operating system may run on the CPU 20A, the auxiliary processor 38, or a mixture of the two. The operating system provides the user with a graphical user interface such as the PlayStation Dynamic Menu. The menu allows the user to access operating system features and to select games and optionally other content.

Accordingly, in a summary embodiment of the present invention a system for evaluating a videogame for a first user comprises at least a first physical input device providing one or physical inputs for use in controlling a videogame (such as for example dual shock 4 controller 43, PlayStation Move controller 42, inputs of a second screen controller such as a PlayStation Vita®, a keyboard 45, or a mouse 46).

The system also comprises a calibration processor (such as CPU 20A) adapted (for example under suitable software instruction) to perform a calibration test using the at least first physical input device to evaluate at least a first physical input capability of the first user with respect to that physical input device.

The system similarly comprises a first evaluation processor (such as CPU 20 A, optionally within a separate entertainment device) adapted (for example under suitable software instruction) to evaluate at the at least first physical input capability exhibited with respect to such a physical input device during reference play of the videogame by one or more reference users other than the first user.

The system again similarly comprises a comparison processor (such as CPU 20 A, optionally within a separate entertainment device) adapted (for example under suitable software instruction) to compare the at least first physical input capability exhibited by the one or more reference users during reference play with that of the first user.

And the system also comprises a second evaluation processor (such as CPU 20 A, optionally within a separate entertainment device) adapted (for example under suitable software instruction) to provide an evaluation of the videogame's suitability for play by the first user, based upon the comparison.

It will also be appreciated that as described above, the system may be adapted for example by suitable software instruction to implement any of the methods and techniques described herein.

The invention claimed is:

1. A method of evaluating a videogame for a first user, comprising the steps of:
   performing a calibration test using a physical input device to evaluate and store data indicative of at least a first physical input capability of the first user with respect to that physical input device prior to the first user engaging in gameplay with the videogame;
   retrieving data indicative of at least a first reference physical input capability exhibited with respect to a corresponding physical input device during at least one reference play-through of the videogame by one or more reference users, other than the first user;
   comparing the data indicative of the at least first reference physical input capability exhibited during the at least one reference play-through with the data indicative of the at least first physical input capability of the first user taken during the calibration test; and
   providing an evaluation to the first user, prior to the user playing the videogame, indicating a suitability of the videogame for play by the first user, based upon the comparison.

2. The method of claim 1, in which the physical input capability of the first user is categorised based upon the evaluation.

3. The method of claim 1, in which the evaluation of the at least first reference physical input capability exhibited during the reference play-through of the videogame is assumed equivalent to a notional standard physical input capability.

4. The method of claim 1, in which separate evaluations are provided to the first user regarding the suitability of the videogame for play by the first user is performed for each of two or more difficulty levels of the videogame.

5. The method of claim 1, in which the evaluation of the suitability of the videogame for play by the first user comprises an evaluation of physical input capability difficulty relative to the user's physical input capability.

6. The method of claim 1, in which the evaluation of the suitability of the videogame for play by the first user comprises one or more of:
   i. an evaluation of the proportions of the game evaluated to be at respective physical input capability difficulties;
   ii an evaluation of respective physical input capability difficulties at a plurality of time or progress intervals during a game; and
   iii. an evaluation of respective physical input capability difficulties at a plurality of locations within a game.

7. The method of claim 1, in which the calibration test is an interactive activity run separate to the videogame.

8. The method of claim 1, in which tested physical input capabilities of the first user include one or more of:
   i. an ability to activate a given input on the physical input device when held normally;
   ii. a time taken to activate a given input on the physical input device in response to a triggering stimulus;
   iii. an ability to activate two or more given inputs on the physical input device simultaneously;
   iv. a time taken to successively activate two or more given inputs on the physical input device in sequence;
   v. an accuracy with which the user can control a variable input controller to provide a target input level, either alone or when also activating one or more other inputs;
   vi. an ability to maintain a consistent target input level for a variable input controller, either alone or when also activating one or other inputs; and
   vii. a range of movement in one or more digits available to the user when holding the physical input device.

9. The method of claim 1, comprising the step of: defining a difficulty mode for a videogame that is within a threshold physical input capability difficulty for the first user or a category of users to whom the first user belongs.

10. The method of claim 1, comprising the steps of:
    evaluating a current suitability of the videogame for play by the first user during gameplay of the videogame; and
    if a current physical input capability difficulty of the videogame relative to the physical input capability of the first user is above a predetermined threshold, implementing an in-game mitigation of that difficulty.

11. The method of claim 10, in which the in-game mitigation comprises one or more of:
   i. remapping one or more in-game controls to a different physical input or sequence of inputs;
   ii. increase a threshold for error tolerance, or speed of actuation of an input or sequence of inputs;
   iii. auto input a predetermined sequence at a predetermined moment within the game;
   iv. reduce, limit or suspend damage taken by the first user;
   v. provide an auto destruct function for in-game obstacles;
   vi. allow the first user to progress to a predetermined safe point.

12. The method of claim 10, in which a graphical indication that the in-game mitigation is being implemented is included with the videogame display.

13. The method of claim 1, in which the availability of a videogame for selection by the first user is responsive to the evaluation of the suitability of the videogame for play by the first user.

14. A non-transitory, computer readable storage medium containing a computer program comprising computer executable instructions, which when executed by a computer system, cause the computer system to perform a method of evaluating a videogame for a first user, comprising the steps of:
   performing a calibration test using a physical input device to evaluate and store data indicative of at least a first physical input capability of the first user with respect to that physical input device prior to the first user engaging in gameplay with the videogame;
   retrieving data indicative of at least a first reference physical input capability exhibited with respect to a corresponding physical input device during at least one reference play-through of the videogame by one or more reference users other than the first user;
   comparing the data indicative of the at least first reference physical input capability exhibited during the at least one reference play-through with the data indicative of the at least first physical input capability of the first user taken during the calibration test; and
   providing an evaluation to the first user, prior to the user playing the videogame, indicating a suitability of the videogame for play by the first user, based upon the comparison.

15. A system for evaluating a videogame for a first user, comprising:
   at least a first physical input device providing one or physical inputs for use by the first user in controlling the videogame;
   a calibration processor adapted to perform a calibration test using the at least first physical input device to evaluate and store data indicative of at least a first physical input capability of the first user with respect to that physical input device prior to the first user engaging in gameplay with the videogame;
   a first evaluation processor adapted to retrieve data indicative of at least a first reference physical input capability exhibited with respect to a corresponding physical input device during at least one reference play-through of the videogame by one or more reference users other than the first user;
   a comparison processor adapted to compare the data indicative of the at least first reference physical input capability exhibited during the at least one reference play-through with the data indicative of the at least first physical input capability of the first user taken during the calibration test; and
   a second evaluation processor adapted to provide an evaluation to the first user, prior to the user playing the videogame, indicating a suitability of the videogame for play by the first user, based upon the comparison.

* * * * *